United States Patent [19]

Van Der Ende

[11] Patent Number: 5,612,989
[45] Date of Patent: Mar. 18, 1997

[54] MEDICAL DIAGNOSTIC AND/OR THERAPEUTIC APPARATUS COMPRISING A C-ARC COMPOSED OF PROFILES

[75] Inventor: Adrianus Van Der Ende, Eindhoven, Netherlands

[73] Assignee: U.S. Philips Corporation, New York, N.Y.

[21] Appl. No.: 571,317

[22] Filed: Dec. 12, 1995

[30] Foreign Application Priority Data

Dec. 12, 1994 [EP] European Pat. Off. ............ 94203595

[51] Int. Cl.⁶ ........................................ A61B 6/06
[52] U.S. Cl. ............................. 378/197; 378/193
[58] Field of Search .................... 378/193, 196, 378/197, 198

[56] References Cited

U.S. PATENT DOCUMENTS

| | | | |
|---|---|---|---|
| 4,866,752 | 9/1989 | Bock et al. | 378/197 |
| 4,955,046 | 9/1990 | Siczek et al. | 378/197 |
| 4,961,214 | 10/1990 | Van Endschot et al. | 378/197 |
| 5,425,068 | 6/1995 | Schaefer et al. | 378/197 |
| 5,426,683 | 6/1995 | O'Farrell, Jr. et al. | 378/197 |
| 5,436,461 | 7/1995 | Saffer et al. | 378/197 X |

FOREIGN PATENT DOCUMENTS 4214858  2/1994  Germany .

*Primary Examiner*—David P. Porta
*Attorney, Agent, or Firm*—Jack D. Slobod

[57] ABSTRACT

A medical diagnostic and/or therapeutic apparatus provided with a C-arc support (2) for, for example an X-ray source (4) and an X-ray detector (6). The support (2) comprises two complementary U-profiles (26) which are connected to one another by way of their flanges (28), using two rod-shaped parts (20) with grooves (24) which extend parallel to the axis of the rod-shaped parts (20) and receive the flanges (28). The flanges (28) are fixed in the grooves (24) by holes (30) which are provided in the rod-shaped parts (20), extend perpendicularly to the plane of the grooves (24), and overlap the grooves (24), in said holes there being arranged pressure pieces (40) which are interconnected by a connection rod (46) which interconnects two oppositely situated pressure pieces (40).

16 Claims, 3 Drawing Sheets

MEDICAL DIAGNOSTIC AND/OR THERAPEUTIC APPARATUS COMPRISING A C-ARC COMPOSED OF PROFILES

BACKGROUND OF THE INVENTION

1. Field of the Invention

The invention relates to a medical diagnostic and/or therapeutic apparatus, comprising a support for diagnostic and/or therapeutic components which is rotatable in its own plane and which is shaped at least partly as a flat arc of circle, the support comprising two complementary profiles, each of which comprises two flanges in perpendicular cross-section, a first and a second flange of a first profile being oriented towards a first and a second flange, respectively, of the second profile, the support comprising a profile connection provided with grooves which extend in the longitudinal direction of the profiles and receive the flanges, the support comprising fixing means for fixing the flanges in the grooves.

2. Description of the Related Art

An apparatus of this kind is known from German Patent DE 42 14 858. The support of the apparatus disclosed therein is composed of two profiles, each of which has a semi-oval or semi-rhombic shape so that in the assembled condition the support has an oval or rhombic cross-section. The two profiles are maintained together by means of a profile connection in the form of a third profile which extends between the first two profiles and which has a barbell-shaped cross-section. In the wide ends of the barbell there are provided grooves which receive the flanges of the semi-oval profiles. The fixing means for fixing the flanges in the grooves are formed by staples or glue, fixing by rolling also being mentioned as a possibility. Regardless of the fixing means chosen, the known apparatus always requires a profile connection of barbell-shaped cross-section so as to receive the flanges of the profiles.

Profile connections of this kind have the drawback of a comparatively complex shape so that, generally speaking, they must be manufactured especially for this purpose by means of a special tool. Because this known profile connection is made of one piece, the flanges of the profiles must be situated at an exact given distance from one another (i.e. the distance between the grooves), because otherwise problems will be encountered during assembly. This imposes severe requirements as regards exactness of the shape of the profiles. Moreover, only one size of profile connection fits a given size of the cross-section of the support, so that various sizes of the profile connection must be stocked for various sizes of the support.

SUMMARY OF THE INVENTION

It is an object of the invention to mitigate these drawbacks by proposing a profile connection which can be more universally used and which enables a firm, rigid connection to be obtained between the profiles and the profile connection so that the support retains the desired rigidity.

To this end, the apparatus in accordance with the invention is characterized in that the profile connection comprises two separate rod-shaped parts which are provided with grooves which extend parallel to the axis of each of the rod-shaped parts.

The dimensions of the rod-shaped parts are highly independent of the dimensions of the support, so that greater flexibility is achieved as regards the stocking for production.

A preferred embodiment of the invention is characterized in that the fixing means are formed by holes which are provided in the rod-shaped parts, extend perpendicularly to the plane of the grooves, and overlap the grooves, pressure pieces being accommodated in said holes, and by transverse connection means for pressing the pressure pieces against the parts of the flanges projecting through the grooves.

These steps offer rigid connection of the flanges in the grooves, imparting the desired mechanical stability to support in that, if desired, the flanges can be deformed by the pressure pieces in the holes. Moreover, these fixing means are highly independent of the dimensions of the support and to some extent independent of the dimensions of the rod-shaped parts, so that the previously mentioned advantages are achieved again. The transverse connection means can be formed by connection rods which interconnect each time two oppositely situated pressure pieces.

In a further embodiment of the invention, the connection rod comprises two collars, each of which is situated at the side of the rod-shaped parts at the inner side of the cavity formed by the profiles.

As a result of this step it is achieved that the connection rod already present is simply also used to ensure suitable dimensional stability of the cross-section of the support; the width of the support in the direction of the connection rod is then determined exclusively by the distance between the collar surfaces which contact the inner side of the rod-shaped parts. The rod-shaped parts are widely commercially available with accurately defined dimensions. Because the inner sides of these rod-shaped parts can be accurately positioned because of the use of the collars, suitably exact external dimensions of the rod-shaped parts are thus also feasible, so that, without requiring further operations, these rod-shaped parts can be used as guide rails for rotation of the support in its own plane.

This distance can be accurately realised in a simple manner.

Further embodiments of the invention are described in the remaining dependent claims.

These and other aspects of the invention will be apparent from and elucidated with reference to the embodiments described hereinafter.

DETAILED DESCRIPTION OF THE PREFERRED EMBODIMENTS

Figure 1:
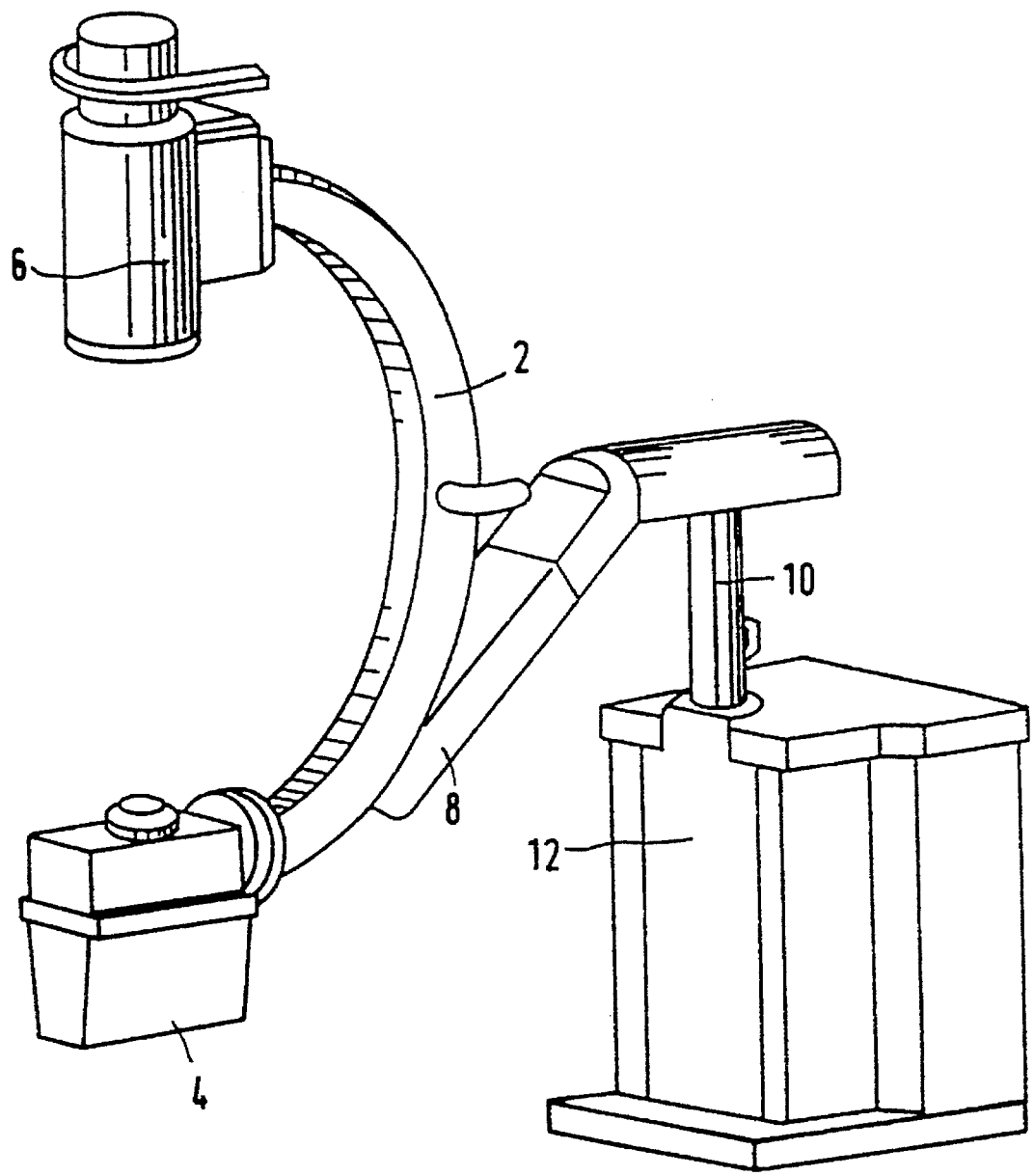
FIG. 1 is a general view of a medical diagnostic and/or therapeutic apparatus in the form of an X-ray apparatus comprising a support for an X-ray source and an X-ray detector.

FIG. 1 is a general view of a medical diagnostic and/or therapeutic apparatus in the form of an X-ray apparatus. The X-ray apparatus comprises a support 2 on which an X-ray source 4 and an X-ray detector 6 are mounted. The support is shaped as an arc of circle, so that the arc can be rotated about an axis extending perpendicularly to the plane of the arc of circle by means of a holder 8. This kind of support is known as a C-arc; generally speaking, they are also rotatable about an axis extending in the plane of the arc of circle. The drive mechanism for this movement is not shown in the Figure. The assembly formed by the support 2 and the holder 8 is also rotatable about a shaft 10. This shaft is mounted on a stand 12 which may be constructed so as to be mobile, if desired. The X-ray source 4 and the X-ray detector 6 are preferably displaceable relative to the support 2. In order to enable easy displacement of these components by hand, they are provided with counterweights (not shown) so that the support must carry a substantial weight. However, it is desired that the support exhibits suitable positioning accuracy, and hence suitable shape stability, in all positions to be occupied by the support. This imposes severe requirements as regards the strength and the rigidity of the support. The invention offers a strong and rigid construction while utilizing parts which can be used for various sizes of the C-arc.

Figure 2A:
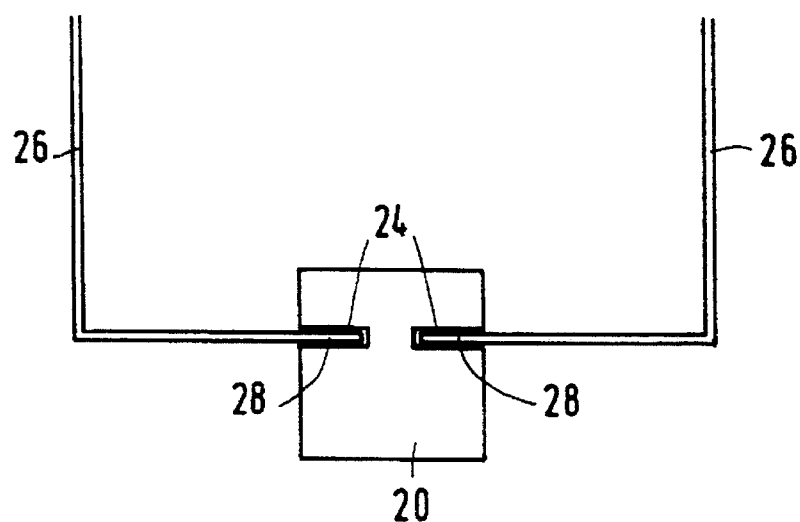
FIG. 2a is a cross-sectional view of rod-shaped parts provided with grooves in accordance with the invention, in which grooves flanges of U-profiles are accommodated.
Figure 2B:
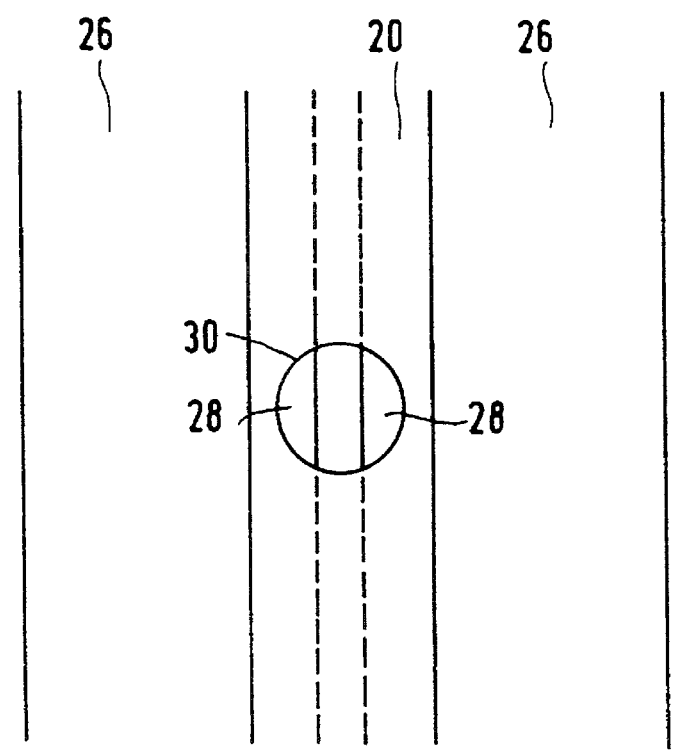
FIG. 2b is a front view of a rod-shaped part in accordance with the invention in which flanges of U-profiles are accommodated and which is provided with a hole for a pressure piece.

FIG. 2a is a perpendicular cross-sectional view of a side of a C-arc in accordance with the invention. The C-arc consists of two U-profiles 26 (for example of aluminium) which are partly shown in the Figure. Each of the U-profiles 26 comprises two flanges, one flange 28 being shown. The two oppositely situated flanges of the U-profiles are accommodated in grooves 28 of a rod-shaped part 20 (for example of aluminium) having a rectangular cross-section. This situation is shown in a side elevation in FIG. 2b. This Figure also shows that the rod-shaped part 20 is provided with a hole 30 which extends perpendicularly to the plane of the grooves 24, and hence also perpendicularly to the plane of the flanges 28. The diameter of this hole is such that it partly overlaps the grooves. Therefore, when the flanges are arranged in the grooves, the ends of the flanges 28 are visible through the hole 30.

Figure 3:
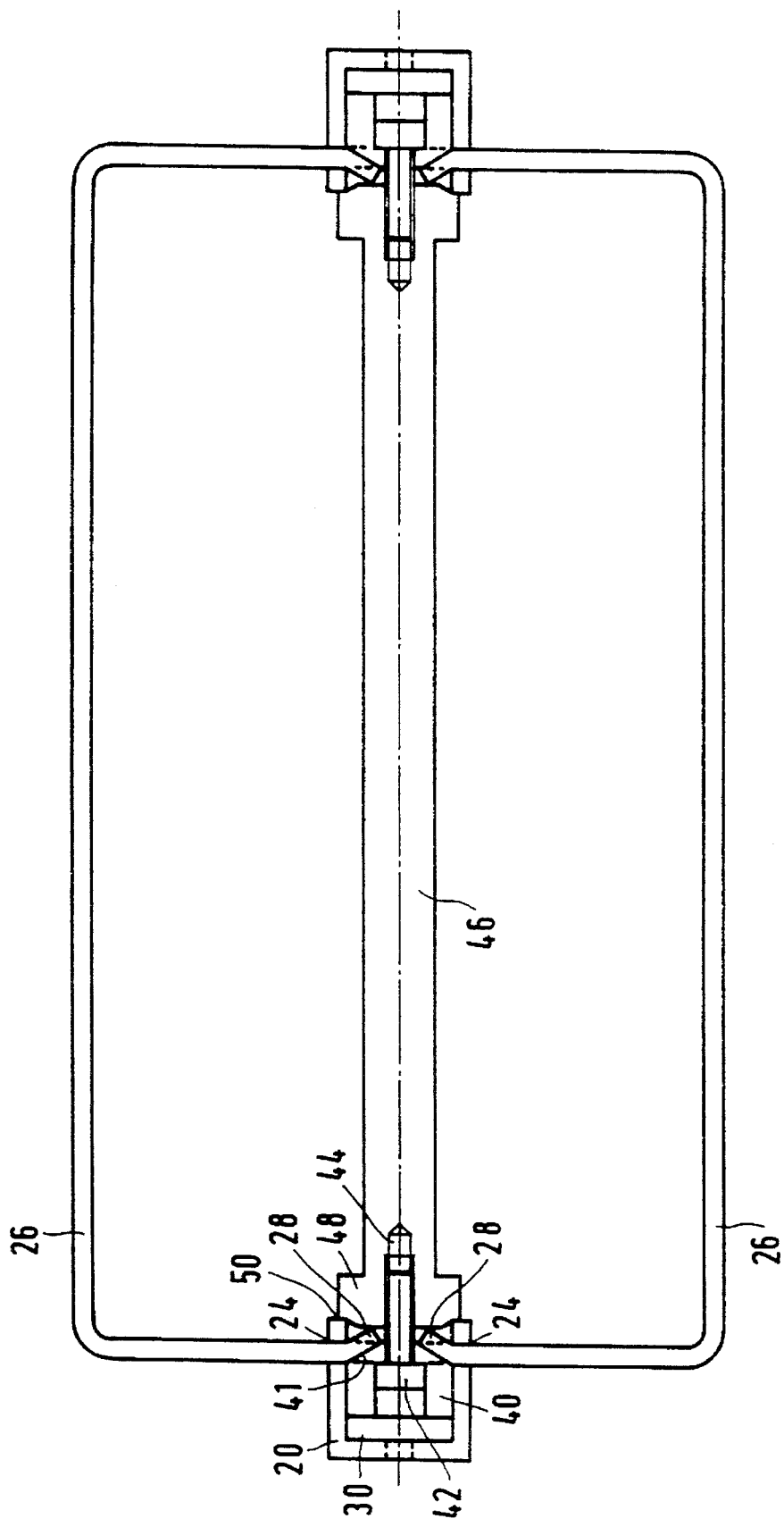
FIG. 3 is a cross-sectional view of the support in accordance with the invention.

FIG. 3 is a complete cross-sectional view of the C-arc in accordance with the invention. The two U-profiles 26 are arranged in two rod-shaped parts 20 by way of their oppositely situated flanges 28. In each rod-shaped part 20 there are provided holes 30 in which a respective pressure piece 40 (made of steel or aluminium) fits. The pressure piece comprises a front side 41 which contacts the flange 28. When the pressure piece 40 is pressed in the direction of the flange 28 with sufficient pressure, the part of the flange 28 which contacts the front 41 will be bent over within the hole 30. Rigid fastening of the U-profiles in the rod-shaped parts 20 is thus achieved. The pressing force on the pressure pieces 40 is created in that transverse connection means in the form of connection rods, such as the rod 46 which interconnects two oppositely situated pressure pieces, are provided between both pairs of flanges. Such a transverse connection rod (made of steel or aluminium) is provided on both sides with a threaded bore 44 in which a bolt 42 can be screwed. The head of the bolt fits in a mating recess in the pressure piece, so that tightening of the bolt 42 forces the pressure piece 40 in the direction of the end of the connection rod 46. At both ends of the connection rod 46 there is provided a respective collar 48, said collars comprising a surface 50 which is conceived to contact the front of the pressure piece 40. The distance between the two surfaces 50 at each end of the connection rod 46 can be readily defined during manufacture; when the pressure pieces are forced into position by the tightening of the bolts 42, the distance between the pressure pieces, i.e. the width of the support, is determined entirely by the distance between the outer surfaces 50 of the collars 48. A sufficiently rigid C-arc is obtained by providing the described construction a sufficient number of times along the circumference of the support 2.

I claim:

1. A medical diagnostic and/or therapeutic apparatus, comprising a support for diagnostic and/or therapeutic components which is rotatable in its own plane and which is shaped at least partly as a flat arc of circle, the support comprising two complementary profiles, each of which comprises two flanges in perpendicular cross-section, a first and a second flange of a first profile being oriented towards a first and a second flange, respectively, of the second profile, the support comprising a profile connection provided with grooves which extend in the longitudinal direction of the profiles and receive the flanges, the support comprising fixing means for fixing the flanges in the grooves characterized in that the profile connection comprises two separate rod-shaped parts which are provided with grooves which extend parallel to the axis of each of the rod-shaped parts.

2. An apparatus as claimed in claim 1, in which the fixing means are formed by holes which are provided in the rod-shaped parts, extend perpendicularly to the plane of the grooves, and overlap the grooves, pressure pieces being accommodated in said holes, and by transverse connection means for pressing the pressure pieces against the parts of the flanges projecting through the grooves.

3. An apparatus as claimed in claim 2, in which the transverse connection means are formed by at least one connection rod which interconnects two oppositely situated pressure pieces.

4. An apparatus as claimed in claim 3, in which the connection rod comprises two collars, each of which is situated at the side of the rod-shaped parts at the inner side of the cavity formed by the profiles.

5. An apparatus as claimed in claim 1, characterized in that at least one of the profiles is constructed as a U-profile.

6. An apparatus as claimed in claim 1, characterized in that at least one of the profiles is made of aluminium.

7. An apparatus as claimed in claim 2, characterized in that at least one of the profiles is constructed as a U-profile.

8. An apparatus as claimed in claim 3, characterized in that at least one of the profiles is constructed as a U-profile.

9. An apparatus as claimed in claim 4, characterized in that at least one of the profiles is constructed as a U-profile.

10. An apparatus as claimed in claim 2, characterized in that at least one of the profiles is made of aluminum.

11. An apparatus as claimed in claim 3, characterized in that at least one of the profiles is made of aluminum.

12. An apparatus as claimed in claim 4, characterized in that at least one of the profiles is made of aluminum.

13. An apparatus as claimed in claim 5, characterized in that at least one of the profiles is made of aluminum.

14. An apparatus as claimed in claim 7, characterized in that at least one of the profiles is made of aluminum.

15. An apparatus as claimed in claim 8, characterized in that at least one of the profiles is made of aluminum.

16. An apparatus as claimed in claim 9, characterized in that at least one of the profiles is made of aluminum.

* * * * *